United States Patent [19]

Graham et al.

[11] Patent Number: 5,621,104
[45] Date of Patent: Apr. 15, 1997

[54] SUBSTITUTED 3-PHENANTHRIDINONE DERIVATIVES AS 5-ALPHA-REDUCTASE INHIBITORS

[75] Inventors: Donald W. Graham, Mountainside; William K. Hagmann, Westfield, both of N.J.

[73] Assignee: Merck & Co., Inc., Rahway, N.J.

[21] Appl. No.: 522,350

[22] PCT Filed: Mar. 22, 1994

[86] PCT No.: PCT/US94/03080

§ 371 Date: Sep. 15, 1995

§ 102(e) Date: Sep. 15, 1995

[87] PCT Pub. No.: WO94/21614

PCT Pub. Date: Sep. 29, 1994

Related U.S. Application Data

[63] Continuation of Ser. No. 36,645, Mar. 24, 1993, abandoned.

[51] Int. Cl.$^6$ .................... C07D 221/12; C07D 401/12
[52] U.S. Cl. .................... 546/108; 546/109; 514/298
[58] Field of Search .................... 546/108, 109; 514/298

[56] References Cited

U.S. PATENT DOCUMENTS

| | | | |
|---|---|---|---|
| 2,227,876 | 1/1941 | Bolt | 546/77 |
| 3,239,417 | 3/1966 | Ditullio et al. | 514/284 |
| 3,264,301 | 8/1966 | Doorenboos et al. | 546/77 |
| 3,285,918 | 11/1966 | Doorenboos et al. | 544/245 |
| 3,567,733 | 3/1971 | Nomine et al. | 546/79 |
| 4,220,775 | 9/1980 | Rasmusson et al. | 546/77 |
| 4,317,817 | 3/1982 | Blohm et al. | 514/150 |
| 4,377,584 | 3/1983 | Rasmusson et al. | 514/284 |
| 4,596,812 | 6/1986 | Chidsey, III et al. | 514/256 |
| 4,732,897 | 3/1988 | Cainelli et al. | 514/228.2 |
| 4,760,071 | 7/1988 | Rasmusson et al. | 514/284 |
| 4,845,104 | 7/1989 | Carlin et al. | 514/284 |
| 4,859,681 | 8/1989 | Rasmusson et al. | 514/284 |
| 4,882,319 | 11/1989 | Holt et al. | 514/119 |
| 4,910,226 | 3/1990 | Holt et al. | 514/573 |
| 5,247,091 | 9/1993 | Mueller-Lehar | 546/105 |

FOREIGN PATENT DOCUMENTS

| | | |
|---|---|---|
| 970692 | 7/1975 | Canada . |
| 0004949 | 10/1979 | European Pat. Off. . |
| 0155096 | 9/1985 | European Pat. Off. . |
| 0200859 | 11/1986 | European Pat. Off. . |
| 0277002 | 6/1988 | European Pat. Off. . |
| 0289327 | 11/1988 | European Pat. Off. . |
| 0314199 | 5/1989 | European Pat. Off. . |
| 0343954 | 11/1989 | European Pat. Off. . |
| 0375344 | 6/1990 | European Pat. Off. . |
| 0375345 | 6/1990 | European Pat. Off. . |
| 0375347 | 6/1990 | European Pat. Off. . |
| 0375349 | 6/1990 | European Pat. Off. . |
| 1465544 | 11/1965 | France . |
| WO91/12261 | 8/1991 | WIPO . |

OTHER PUBLICATIONS

Campbell et al., Syn. Commun. (1979), vol. 9, pp. 471–476, "A Novel Synthesis . . . : An Intermediate Useful in Terpene Synthesis".

Vila et al., Tet. Letters (1989), vol. 45, pp. 4951–4960, "Conformational Analysis of the 4a–Methyl Octahydrophenanthrene System".

Iida et al., Heterocycles (1983), vol. 20, pp.227–230, "A New Synthesis of Phenanthridine Derivatives".

Schultz et al., J. Am. Chem. Soc. (1978), vol. 100, pp. 2140–2149, "Heteroatom Directed Photoarylation. Synthetic Potential of the Heteroatom Sulfur".

Neri et al., Endo. (1972), vol. 91, No. 2, pp. 427–437, "A Biological Profile of a Non–steroidal Antiandrogen, SCH 13521 . . . ".

Nayfeh et al., Steroids, vol. 14 (1969), pp. 269–283, "Metabolism of Progesterone by Rat Testicular Homogenates–III".

Voight et al., Endo., vol. 92 (1973), p.1216, "The Antiandrogenic Action of 4–Androsten–3–one–17beta–Carboxylic Acid and its Methyl Ester on Hamster Flank Organ".

Doorenbos et al., J. Pharm. Sci., vol. 62, No. 4 (1973), pp. 638–640, "Synthesis & Antimicrobial Properties of 17Beta–Isopentyloxy–4–Aza–5 Alpha–Androstane and the 4–Methyl Derivative".

Doorenbos et al., J. Pharm. Sci., vol. 60, No. 8 (1971), pp. 1234–1235, "4,17 Alpha–Dimethyl–4–Aza–5 Alpha–Androstan–17 beta–ol Acetate & Related Azasteroids".

Doorenbos et al., J. Pharm. Sci., vol. 63, No. 4 (1974), pp. 620–622, "Synthesis & Evaluation of Antimicrobial Properties of Amidinoazaandrostanes and Guanidinoazaandrostanes".

Rasmusson et al., J. Med. Chem., vol. 29, No.11 (1986), pp. 2298–3115, "Aza Steroids: Structure–Activity Relationships . . . ".

Brooks et al., Prostate, vol. 9, No. 1 (1986), pp. 65–75, "Prostatic Effects Induced in Dogs by . . . 5 alpha–Reductase Inhibitors".

Brooks et al., Steroids, vol. 47, No. 1 (1986), pp. 1–19, "5 Alpha–Reductase Inhibitory . . . Activities of Some 4–Aza–Steroids in the Rat".

Liang et al., Endo., vol. 117, No. 2, (1986), pp. 571–579, "Species Differences in Prostatic Steroidal 5 Alpha–Reductases of Rat, Dog and Human".

(List continued on next page.)

Primary Examiner—Alan L. Rotman
Assistant Examiner—A. Rotman
Attorney, Agent, or Firm—Catherine D. Fitch; Melvin Winokur

[57] ABSTRACT

The present invention provides for the preparation of compounds, namely, 3-phenanthridinones and their derivatives and their unique ability to inhibit 5-alpha-reductase or their isozymes thereof in mammals enabling said compounds for treating hyperandrogenic conditions of acne, androgenic alopecia, male pattern baldness, female hirsutism, benign prostatic hyperplasia, prostatitis and prostatic cancer.

1 Claim, No Drawings

OTHER PUBLICATIONS

Rasmusson et al., J. Med. Chem., vol. 27, No. 12 (1984), pp. 1690–1701, "Azasteroids as Inhibitors of Rat Prostatic 5 Alpha–Reductase".

Back et al., J. Org. Chem, vol. 46, No. 7 (1981), pp. 1442–1446, "N–Chloroazasteroids . . . ".

Liang et al., Chem. Abstracts, vol. 95, 109055j, "Inhibition of 5–Alpha–Receptor Binding . . . by a 4–Methyl–4–Aza–Steroid" (1985).

Kadohama et al., JNCL, vol. 74, No. 2 (Feb. 1985), pp. 475–481, "Retardation of Prostate Tumor Progression in the Noble Rat by 4–Methyl–4–Aza–Steroidal Inhibitors of 5 Alpha–Reductase".

Andriole et al., The Prostate, vol. 10 (1987), pp. 189–197, "The Effect of 4MA . . . on the Growth of . . . Human Tumors . . . ".

Bingham et al., J. Endocr., vol. 57 (1973), pp. 111–121, "The Metabolism of Testosterone by Human Male Scalp Skin".

Kedderis et al., Toxicol. Appl. Pharmacol., vol. 103 (1990), pp. 222–227, "Studies with Nitrogen–Containing Steroids . . . ".

Metcalf et al., Bioinorganic Chemistry, vol. 17 (1986), pp. 372–376, "Patent Inhibition of Human Steroid . . . by 3–Androstene–3–Carboxylic Acid".

Levy et al., Biochemistry, vol. 29 (1990), pp. 2815–2824, "Inhibition of Rat Liver Steroid 5 Alpha–Reductase . . . ".

Holt et al., J. Med. Chem., vol. 33 (1990), pp. 943–950, "Steroidal A Ring Carboxylic Acids . . . ".

Levy et al., J. Steroid Biochem., vol. 34, No. 1–6 (1989), pp. 571–575, "Interaction Between Rat Prostatic 5 Alpha–Reductase . . . ".

Holt et al., J. Med. Chem., vol. 33 (1990), pp. 937–942, "Steroidal A Ring Aryl Carboxylic Acids . . . ".

Metcalf et al., TIPS (Dec. 1989), vol. 10, pp. 491–495, "Inhibitors of . . . 5 Alpha–Reductase in Benign Prostatic Hyperplasia . . . ".

Murphy et al., Steroids, vol. 35, No. 3 (Mar. 1980), pp. 1–7, "Effect of Estradiol on a . . . Binding Protein in the Uterus of the Mouse".

Stone et al., Prostate, vol. 9 (1986), pp. 311–318, "Estrogen Formation in Human Prostatic Tissue . . . ".

Brooks et al., Steroids, vol. 47, No. 1 (1986), pp. 1–19, "5 Alpha–Reductase Inhibitory . . . Activities of Some 4–Azasteroids . . . ".

Labrie et al., Lancet, No. 8515 (1986), pp. 1095–1096, "Combination Therapy in Prostate Cancer".

Rittmaster et al., J. Clin. Endocrin & Metab., vol. 55, No. 1 (1987), pp. 188–193, "The Effects of . . . a 5 Alpha–Reductase Inhibitor . . . ".

Diani et al., J. Clin. Endoc. & Metab., vol. 74, No. 2 (1990), pp. 345–350, "Hair Growth Effects of Oral Administration of Finasteride . . . ".

Bruchovsky et al., J. Clin. Endoc. Metab., vol. 67, No. 4 (1988), pp. 808–816, "Kinetic Parameters of 5 Alpha–Reductase Activity in Stroma & Epithelium of Normal, Hyperplastic & Carcinomatous Human Prostates".

Hudson, J. Steroid Biochem., vol. 26, No. 3 (1987), pp. 349–353, "Comparison of Nuclear 5 Alpha–Reductase Activities in the Stromal and Epithelial Fractions of Human Prostatic Tissue".

Moore et al., J. Biol. Chem., vol. 251, No. 19 (1976), pp. 5895–5900, "Steroid 5 Alpha–Reductase in Cultured Human Fibroblasts".

Andersson et al., J. Biol. Chem., vol. 264, No. 27 (1989), pp. 16249–16255, "Expession Cloning & Regulation of Steroid 5 Alpha–Reductase, an Enzyme Essential for Male Sexual Differentiation".

Andersson et al., Proc. Nat'l Acad. Science, vol. 87 (1990), pp. 3640–3644, "Structural & Biochemical Properties of Cloned and Expressed Human and Rat Steroid 5 Alpha–Reductases".

Andersson et al., Nature, vol. 354 (Nov. 14, 1991), pp. 159–161, "Deletion of Steroid 5 Alpha–Reductase–2 Gene in Male Pseudohermaphroditism".

Wilson, Biol. of Reproduction, vol. 46 (1992), pp. 168–173, "Syndromes of Androgen Resistance".

Geldolf et al., Eur. J. Cancer, vol. 26, No. 2 (1990), pp. 188, "Enzyme Inhibitors in Hormone Dependent Prostate Cancer Growth".

Geldolf et al., J. Cancer Res. Clin. Oncol., vol. 118 (1992), pp. 50–55, "Consideration of the Use of . . . 4MA . . . in Prostate Cancer Research".

Brooks et al., The Prostate, vol. 18 (1991), pp. 215–227, "Effect of Castration, DES, Flutamide, and MK–906 on Growth of the Dunning Rat Prostatic Carcinoma".

Jones et al., J. Med. Chem., vol. 36 (1993), pp. 421–423, "Nonsteroidal Inhibitors of Human Type 1 Steroid 5alpha–Reductase".

Masubuchi et al., Eur. J. Pharm., vol. 183, No. 5 (1990), p. 1757, "Lack of DHT Inhibition . . . by Treatment of 4MA . . . ".

SUBSTITUTED 3-PHENANTHRIDINONE DERIVATIVES AS 5-ALPHA-REDUCTASE INHIBITORS

CROSS-REFERENCE

This application is a 371 of PCT/US94/03080 filed Mar. 22, 1994, which is a continuation of Ser. No. 08/036,645 filed Mar. 24, 1993, (now abandoned).

FIELD OF THE INVENTION

The present invention provides novel compounds, novel compositions, methods of their use and methods of their manufacture, where such compounds are generally pharmacologically useful as agents in therapies whose mechanism of action rely on the selective inhibition of the isozyme 5α-reductase 1.

BACKGROUND OF THE INVENTION

Certain undesirable physiological manifestations, such as acne vulgaris, seborrhea, female hirsutism, male pattern baldness (alopecia) and benign prostatic hyperplasia, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endocrinol. 1972, 91 (2). However, these products, though devoid of hormonal effects, compete with all natural androgens for receptor sites, and hence have a tendency to feminize a male host or the male ferns of a female host and/or initiate feed-back effects which would cause hyperstimulation of the testes.

The principal mediator of androgenic activity in some target organs, e.g. the prostate, is 5α-dihydrotestosterone, formed locally in the target organ by the action of testosterone-5α-reductase. Inhibitors of testosterone-5α-reductase will serve to prevent or lessen symptoms of hyperandrogenic stimulation in these organs. It is now known that a second 5α-reductase isozyme exists, which interacts with epidermal tissues, especially in scalp tissues. This form is conventionally designated as 5α-reductase 1, while the isozyme that principally interacts with the prostatic tissues is designated as 5α-reductase 2. Both isozymes are active in the prostatic tissues. Thus, in the treatment of hyperandrogenic disease conditions e.g. benign prostatic hyperplasia (BPH), it would be desirable to have one drug entity which is active against both isozymes in the prostate to significantly inhibit dihydrotesterone production, while also having another drug entity which is highly selective for inhibiting the isozyme 5α-reductase 1 associated with the scalp, for use in treating conditions of the skin and scalp, e.g. acne and alopecia in males and hirsutism in females. Additionally, such a selective 5α-reductase 1 inhibitor could also be used in combination with finasteride (PROSCAR®), which is highly selective for 5α-reductase 2, for combination therapy in the treatment of BPH. Therefore it is an object of this invention to provide compounds that have sufficient activity in the inhibition of one or both 5α-reductase isozymes. It is an additional object of this invention to provide compounds that are useful in the treatment and/or prevention of benign prostatic hyperplasia. It is an additional object of this invention to provide compounds that are useful in the treatment of female hirsutism, male pattern baldness, acne, androgenetic alopecia, prostatic cancer, and insufficient plasma levels of high density lipoproteins. The compounds of the invention have utility in one or more of the aforementioned areas.

SUMMARY OF THE INVENTION

The compounds of the present invention are those of the general structural formula I:

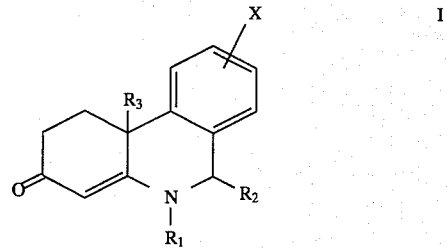

or a pharmaceutically acceptable salt or ester thereof, wherein $R_1$ and $R_3$ are independently selected from the group consisting of hydrogen and $C_{1-6}$ alkyl;

$R_2$ is selected from the group consisting of hydrogen, $C_{1-6}$ alkyl, $C_{1-6}$ alkoxyl and $C_{1-6}$ alkylcarbonyloxy;

X is selected from the group consisting of hydrogen, $C_{1-6}$ alkyl, $C_{1-6}$ alkoxyl, $C_{1-6}$ alkoxy-$C_{1-6}$ alkyl, halogen, cyano, $C_{1-6}$ alkylcarbonyl, Ar-carbonyl, $C_{1-6}$ alkoxycarbonyl, $C_{1-6}$ alkylaminocarbonyl, Ar-aminocarbonyl and di-$C_{1-6}$ alkylaminocarbonyl; and Ar is phenyl or pyridyl.

DETAILED DESCRIPTION OF THE INVENTION

Salts encompassed within the term "pharmaceutically acceptable salts" refer to non-toxic salts of the compounds of this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulariate | N-methylglucamine ammonium salt |
| Citrate | |
| Dihydrochloride | Oleate |
| Edetate | Oxalate |
| Edisylate | Pamoate (Embonate) |
| Estolate | Palmitate |
| Esylate | Pantothenate |
| Fumarate | Phosphate/diphosphate |
| Gluceptate | Polygalacturonate |
| Gluconate | Salicylate |
| Glutamate | Stearate |
| Glycollylarsanilate | Sulfate |
| Hexylresorcinate | Subacetate |
| Hydrabamine | Succinate |
| Hydrobromide | Tannate |

| | |
|---|---|
| Hydrochloride | Tartrate |
| Hydroxynaphthoate | Teoclate |
| Iodide | Tosylate |
| Isothionate | Triethiodide |
| Lactate | Valerate |

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any specified numbers within this range.

Whenever the term "alkyl" or its prefix root appears in a name of a substituent (e.g. aralkoxyaryloxy) it shall be interpreted as including those limitations given above for "alkyl".

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as an antiandrogenic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0 and 50.0 mg of active ingredient. Effective plasma levels of the compounds of the present invention range from 0.002 mg to 50 mg per kg of body weight per day. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen. Other preferred topical preparations include creams, ointments, lotions, aerosol sprays and gels, wherein the concentration of active ingredient would range from 0.1% to 15%, w/w or w/v.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds of the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail.

Synthesis Scheme I

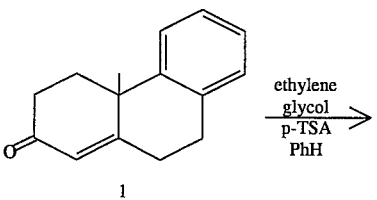

1

5
-continued
Synthesis Scheme I

6
Synthesis Scheme II

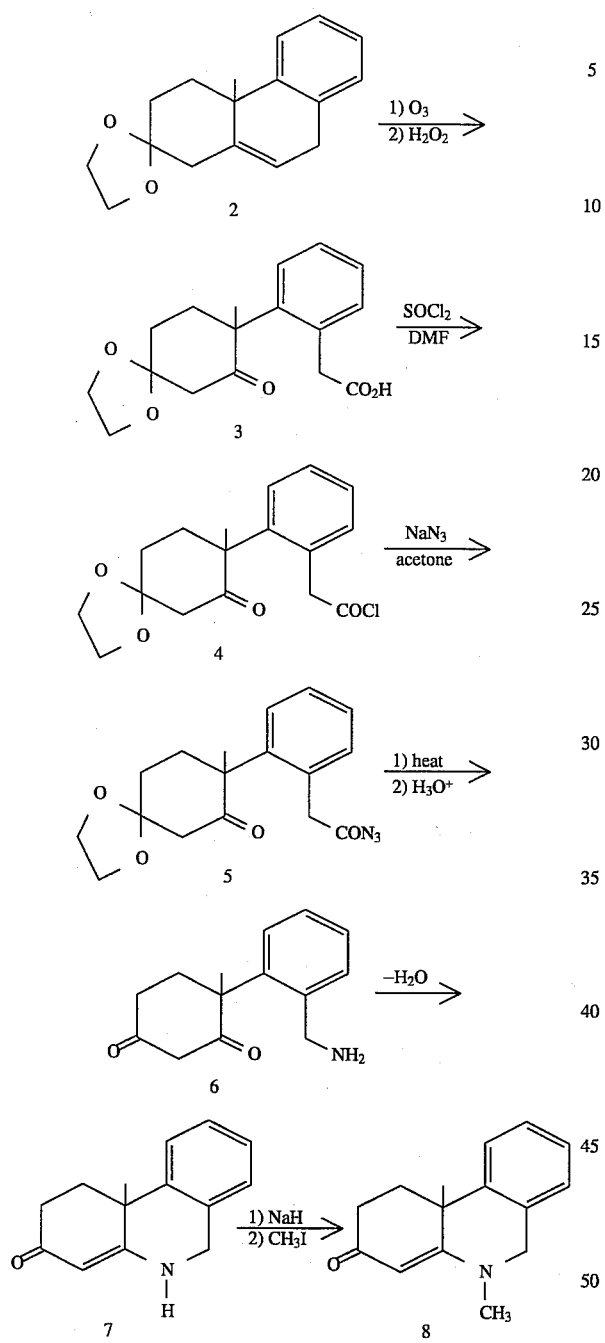

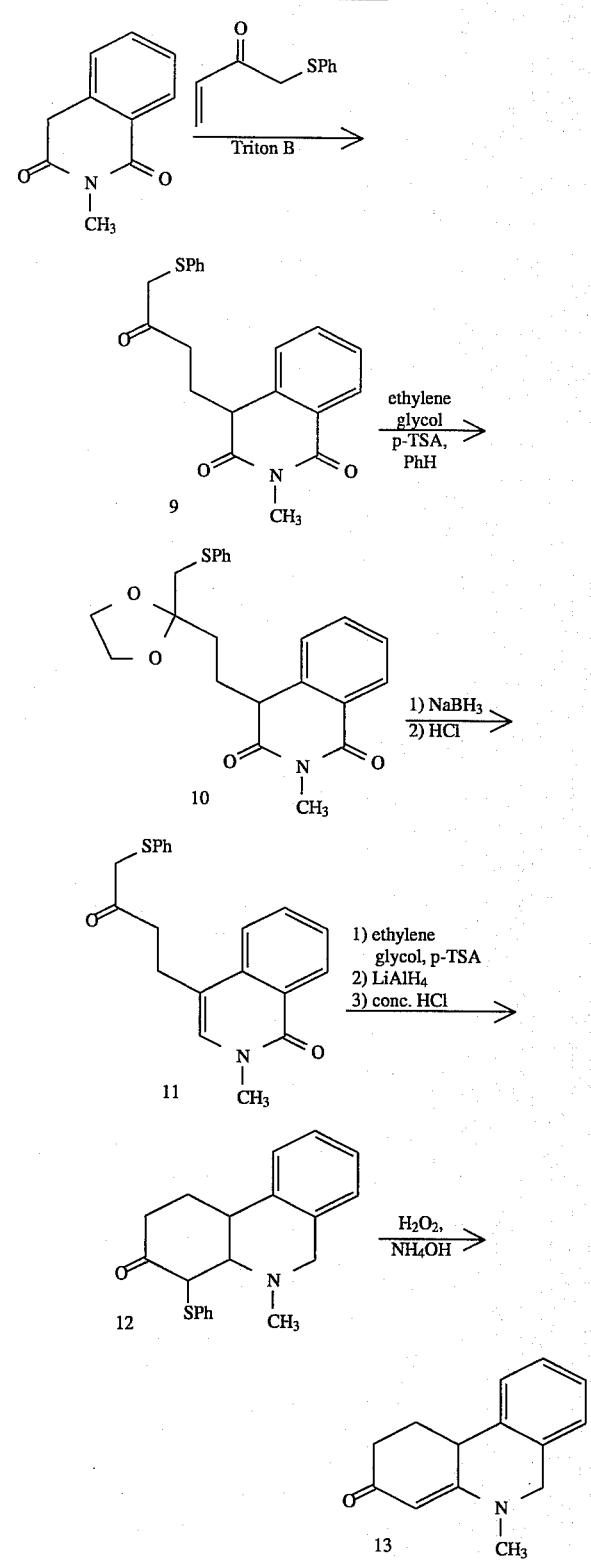

The carbonyl of a phenanthrone such as 1 is protected as the ketal 2 by reaction with ethylene glycol in the presence of an acid with removal of water. The double bond which moves out of conjugation with the aforementioned carbonyl is oxidized to the ozonide which is subsequently oxidized with hydrogen peroxide. The resulting acid 3 is converted to the acyl azide 5 via the acid chloride 4. Heating of 5 results in a Curtius rearrangement to the isocyanate which, along with the ketal protecting group, is hydrolyzed in the presence of aqueous acid to the dione 6 which will spontaneously cyclize to the 3-phenanthridinone 7. Alkylation of the nitrogen with an alkyl iodide results in the formation of 8.

In Scheme II, Michael addition of N-alkyl homophthalimide to phenylthiomethyl vinyl ketone in the presence of base gives the adduct 9. The side chain carbonyl is protected as the ketal and one of the ring carbonyl groups is reduced with sodium borohydride and eliminated to form the isocarbostyril or isoquinolone-like compound 11. Subsequent ketalization of the side chain carbonyl followed by reduction and cyclization yields the substituted 3-phenanthridinone 12. Oxidative elimination of the phenylthio group gives the desired product 13.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

EXAMPLE 1

BIOLOGICAL ASSAYS

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25 M sucrose using a Potter-Elvehjem homogenizer. A crude nuclear pellet was prepared by centrifugation of the homogenate at 1,500 xg for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay

The reaction mixture contained in a final volume of 100 μl is: 40 mM buffer (human scalp, potassium phosphate, pH 6.5; human prostatic 5α-reductase, sodium citrate, pH 5.5), 0.3–10 μM $^{14}$C-T (or $^{3}$H-T), 1 mM DTT, and 500 μM NADPH. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times DHT, 6.8–7.2 min; androstanediol, 7.6–8.0; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

EXAMPLE 2

A solution of 4a-methyl-4,4a,9,10-tetrahydro-2(3H)-phenanthrone 1 (7 g, 33 mmol; prepared by the method of A. L. Campbell and J. D. McChesney, Syn. Commun. 1979, 9, 471–479) is dissolved in anhydrous benzene (300 mL) and ethylene glycol (16 mL) and p-toluenesulfonic acid (0.7 g, 4 mmol) added. The solution is refluxed with the removal of water in a Dean-Stark trap according to the method of A. J. Vila, R. A. Spanevello, A. C. Olivieri, M. G. Sierra, and J. D. McChesney, Tet. Lett. 1989, 45, 4951–4960 to form the ketal, 2-ethylenedioxy-4a-methyl- 1,2,3,4,4a,9-hexahydrophenanthrene 2.

A solution of 2 is dissolved in methylene chloride and cooled to −78° C. and a stream of ozone is passed through it until a pale blue color persists. A solution of water containing 30% hydrogen peroxide is added and the mixture warmed to 0° C. for 2 hr, then to room temperature for 48 hr. Ethyl acetate is added and the solution successively washed with 2% aqueous sodium bisulfite solution, water, and saturated salt solution. The organic solution is dried over anhydrous sodium sulfate and the solvent removed by rotoevaporation to yield 2-(4'-ethylenedioxy-1 '-methyl-2'-oxocyclohexyl)-phenylacetic acid 3.

The acid 3 is dissolved in diethyl ether and dimethylformamide and thionyl chloride is added. The solution is stirred at room temperature for 1 hr and poured into ice water. The ether layer is separated and dried over anhydrous sodium sulfate. The solvent is removed by rotoevaporation and the product, 2-(4'-ethylenedioxy-1'-methyl-2'-oxocyclohexyl)-phenylacetyl chloride 4, is dissolved in acetone. Sodium azide is added and the solution stirred for 20 min. Water is added and the mixture extracted with diethyl ether and the organic layer dried over anhydrous sodium sulfate. The solvent is removed by rotoevaporation to yield 2-(4'-ethylenedioxy-1'-methyl-2'-oxocyclohexyl)-phenylacetyl azide 5.

The acyl azide 5 is dissolved in dimethylformamide and heated to 100° C. until nitrogen evolution ceases. The solution is cooled and treated with aqueous acetic acid to form 2-(2', 4'-dioxo-1'-methyl-cyclohexyl)-benzyl amine 6. Diethyl ether is added and the solution is washed successively with saturated sodium bicarbonate solution, water, and saturated salt solution and dried over anhydrous sodium sulfate. The solvent is removed by rotoevaporation to yield 1,2,3,4,4a,5,6,10b-octahydro- 10b-methyl-3-phenanthridinone 7.

A solution of 7 in dimethylformamide at 0° C. is treated with 1 equivalent of sodium hydride followed by methyl iodide. After stirring at room temperature, diethyl ether is added and the solution successively washed with water and saturated salt solution. The solvent is removed by rotoevaporation to yield 1,2,3,4,4a,5,6,10b-octahydro-5,10b-dimethyl-3-phenanthridinone 8.

EXAMPLE 3

3(2H)-Phenanthridinone derivatives have been prepared from homophthalimide by the method of H. Iida et al., (Heterocycles 1983, 20, 227–30). 2-Methyl-homophthalimide is reacted with phenylthiomethyl vinyl ketone (prepared by the method A. G. Schultz et al.,J. Am. Chem. Soc. 1978, 100, 2140–9) in the presence of Triton B according to the described method to form 2-methyl-4-(3'-oxo-4'-phenylthiobutyl)-homophthalimide 9.

Reaction of 9 with ethylene glycol and p-toluenesulfonic acid in refluxing anhydrous benzene with removal of water by a Dean-Stark trap gives 4-(3'-ethylenedioxy-4'-phenylthiobutyl)-2-methylhomophthalimide 10 which is reduced with sodium borohydride and treated with aqueous hydrochloric acid to form 2-methyl-4-(3'-oxo-4'-phenylthiobutyl)-isocarbostyril 11.

Ketalization of 11 with ethylene glycol in the presence of p-toluenesulfonic in reluxing benzene follows as above. Reaction of the ketal with lithium aluminum hydride in diethyl ether followed by treatment with concentrated hydrochloric acid at 100° C. gives 5-methyl-1,2,3,4,4a,5,6, 10b-octahydro-4-phenylthio-3-phenanthridinone 12. Treatment of 12 with basic hydrogen peroxide gave 5-methyl-1, 2,3,4,4a, 10b-hexahydro-3-phenanthridinone 13.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims Be interpreted as broadly as is reasonable.

What is claimed is:

1. A compound of the formula I

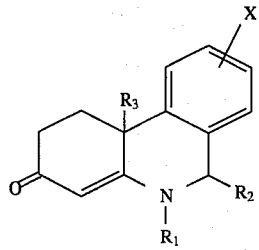

or a pharmaceutically acceptable salt or ester thereof, wherein $R_1$ and $R_3$ are independently selected from the group consisting of hydrogen and $C_{1-6}$ alkyl;

$R_2$ is selected from the group consisting of hydrogen, $C_{1-6}$ alkyl, $C_{1-6}$ alkoxyl and $C_{1-6}$ alkylcarbonyloxy;

X is selected from the group consisting of hydrogen, $C_{1-6}$ alkyl, $C_{1-6}$ alkoxyl, $C_{1-6}$ alkoxy-$C_{1-6}$ alkyl, halogen, cyano, $C_{1-6}$ alkylcarbonyl, Ar-carbonyl, $C_{1-6}$ alkoxycarbonyl, $C_{1-6}$ alkylaminocarbonyl, Ar-aminocarbonyl and di-$C_{1-6}$ alkylaminocarbonyl; and Ar is phenyl or pyridyl.

* * * * *